(12) United States Patent
Edwards et al.

(10) Patent No.: US 7,449,441 B2
(45) Date of Patent: Nov. 11, 2008

(54) LIQUID COMPOSITION FOR REDUCING TOILET ODOR

(75) Inventors: William Edwards, Aiea, HI (US); Derek Edwards, Chesterton, IN (US); Frederick E. Edwards, Valparaiso, IN (US)

(73) Assignee: Toilex, LLC, Valparaiso, IN (US)

( * ) Notice: Subject to any disclaimer, the term of this patent is extended or adjusted under 35 U.S.C. 154(b) by 0 days.

(21) Appl. No.: 11/419,025

(22) Filed: May 18, 2006

(65) Prior Publication Data

US 2006/0264348 A1     Nov. 23, 2006

Related U.S. Application Data

(60) Provisional application No. 60/594,915, filed on May 18, 2005.

(51) Int. Cl.
    *C11D 17/00* (2006.01)
(52) U.S. Cl. .................. 510/506; 510/191; 510/476; 510/505
(58) Field of Classification Search ............ 510/191, 510/476, 505, 506
    See application file for complete search history.

(56) References Cited

U.S. PATENT DOCUMENTS

| | | | |
|---|---|---|---|
| 3,951,893 A | 4/1976 | Gander | |
| 4,145,226 A * | 3/1979 | Neuhaus | 106/287.24 |
| 5,024,780 A * | 6/1991 | Leys | 510/174 |
| 5,081,104 A * | 1/1992 | Orson, Sr. | 512/3 |
| 5,290,954 A * | 3/1994 | Roberts et al. | 549/233 |
| 5,707,961 A * | 1/1998 | Bajgrowicz et al. | 512/17 |
| 5,912,223 A * | 6/1999 | Drapier | 510/417 |
| 6,180,595 B1 * | 1/2001 | Van Walsum et al. | 512/3 |
| 6,376,443 B1 * | 4/2002 | Julemont | 510/238 |
| 6,475,967 B1 * | 11/2002 | Arvanitidou et al. | 510/235 |
| 6,506,723 B1 * | 1/2003 | Walsum et al. | 512/1 |
| 6,596,681 B1 * | 7/2003 | Mahieu et al. | 510/438 |
| 6,762,157 B1 * | 7/2004 | Babinski et al. | 510/101 |
| 6,835,678 B2 | 12/2004 | Jackson et al. | |
| 6,835,705 B2 * | 12/2004 | Shaukat et al. | 510/417 |
| 6,849,586 B2 * | 2/2005 | Avery et al. | 510/191 |
| 6,949,495 B2 * | 9/2005 | Suto et al. | 510/175 |
| 2002/0141962 A1 * | 10/2002 | Watanabe et al. | 424/76.1 |
| 2003/0068295 A1 * | 4/2003 | Rohde et al. | 424/76.1 |
| 2005/0048397 A1 * | 3/2005 | Jo et al. | 430/256 |
| 2005/0272621 A1 * | 12/2005 | Chae et al. | 510/175 |
| 2006/0167064 A1 * | 7/2006 | Seth | 514/345 |

FOREIGN PATENT DOCUMENTS

JP          2003026595      *   1/2003

* cited by examiner

*Primary Examiner*—Gregory E Webb
(74) *Attorney, Agent, or Firm*—Hartman & Hartman, P.C.; Gary M. Hartman; Domenica N. S. Hartman

(57) ABSTRACT

A composition capable of eliminating or at least reducing toilet odor when applied directly to the water contained in the toilet bowl prior to use. The liquid composition comprises about 60 to about 70 weight percent diethylene glycol monoethyl ether ($CH_2OHCH_2OCH_2CH_2OC_2H_5$), the balance being at least additional constituent, such as fragrances and/or stabilizers.

5 Claims, No Drawings

LIQUID COMPOSITION FOR REDUCING TOILET ODOR

CROSS REFERENCE TO RELATED APPLICATIONS

This application claims the benefit of U.S. Provisional Application No. 60/594,915, filed May 18, 2005, the contents of which are incorporated herein by reference.

BACKGROUND OF THE INVENTION

The present invention generally relates to methods and compositions for eliminating toilet odor by direct application of a composition to the water contained in the toilet bowl prior to use.

A product under the name "Powerful One-Drop" is commercially available from Kobayashi Pharmaceutical Co., Ltd., of Japan for eliminating toilet odor by adding the product to the water in a toilet bowl after use, optionally prior to use. According to the information provided on its packaging, this product contains fragrances, plant extract, and glycol ether (dipropylene glycol monomethyl ether also known as (2-methoxymethylethoxy)-propanol; $(CH_3(OC_3H_6)_2OH$; CAS Number 34590-94-8). Another product of this type is available from Prelam Enterprises Ltd. of Moncton, New Brunswick, Canada, under the name "Just' a Drop." The ingredients of this product have been described in literature as a plant extract, disinfectant, and perfume.

BRIEF SUMMARY OF THE INVENTION

The present invention provides a liquid composition capable of eliminating or at least reducing toilet odor when applied directly to the water contained in the toilet bowl prior to use. The liquid composition comprises about 60 to about 70 weight percent diethylene glycol monoethyl ether $(CH_2OHCH_2OCH_2CH_2OC_2H_5$; also known as diglycol monoethyl ether, etc.; CAS No. 111-90-0), the balance being one or more additional constituents, such as fragrances and/or stabilizers. According to particular and preferred aspects of the invention, the liquid composition does not contain dipropylene glycol monomethyl ether. Furthermore, the preferred liquid composition of this invention appears to react with water, in that droplets of the composition placed in water appear to roil in the water before forming a sheen on the water surface.

When used in an effective amount, typically about two to four droplets, to the water in a typical toilet bowl, the sheen formed by the liquid composition of this invention is sufficient to cover essentially the entire surface of the water. Thereafter, toilet odors emanating from the toilet bowl are drastically reduced if not eliminated during and following subsequent toilet usage.

Other objects and advantages of this invention will be better appreciated from the following detailed description.

DETAILED DESCRIPTION OF THE INVENTION

As noted above, the present invention provides a liquid composition capable of reducing toilet odors when applied directly to water contained in a toilet bowl prior to use of the toilet bowl. In a preferred embodiment, the liquid composition consists of about 60 to about 70 weight percent diethylene glycol monoethyl ether, at least one stabilizer, and optionally but preferably additional constituents such as fragrances.

Testing has evidenced that the ratio of the diethylene glycol monoethyl ether to the remainder of the constituents is critical. Suitable results have been obtained with the composition formulated to contain 60 to 70 weight percent diethylene glycol monoethyl ether, with the balance fragrances and an effective amount of stabilizer (e.g., about 0.5 weight percent). Compositions containing diethylene glycol monoethyl ether outside this range have not been effective. Optimal results appear to be obtained with the composition containing about 65 weight percent diethylene glycol monoethyl ether, about 34.5 weight percent fragrances, and about 0.5 weight percent of a stabilizer commercially available under the names Optical Bright Benetex OB-EP or Optiblanc ATR Liquid. These stabilizers are believed to contain about 40 to about 50 weight percent dipropylene glycol monomethyl ether (also known as 2-methoxymethylethoxy)-propanol; $(CH_3(OC_3H_6)_2OH$; CAS No. 34590-94-8), about 40 to about 50 weight percent ethoxylated alkyl phenol, and less than 2 weight percent of a coumarin derivative.

Various fragrances can be used in the liquid composition of this invention. Two fragrances successfully used in combination are proprietary fragrances available through WholesaleSuppliesPlus.com (North Royalton, Ohio) under the names "Lavender Breeze" and "Christmas Wreath Yankee Type." In the composition noted above as containing about 65 weight percent diethylene glycol monoethyl ether, about 34.5 weight percent fragrances, and about 0.5 weight percent of a stabilizer, the "Lavender Breeze" and "Christmas Wreath Yankee Type" fragrances constituted about 11.5 and about 23.0 weight percent, respectively, of the total composition. In addition to fragrances, it is foreseeable that other additives could be included in the liquid composition to provide various performance, processing, or economic benefits.

When used in an effective amount, typically about two to four droplets to standing water in a typical toilet bowl, the liquid composition of this invention appears to react with water, presumably from the diethylene glycol monoethyl ether content of the composition, in that droplets of the composition appear to roil in the water (a reaction that is believed not to occur with compositions containing dipropylene glycol monomethyl ether). Thereafter, a sheen appears on the water surface. Normal use of the toilet can then proceed, during and after which normal toilet odors are greatly reduced if not eliminated.

While the invention has been described in terms of a preferred embodiment, it is apparent that other forms could be adopted by one skilled in the art. Therefore, the scope of the invention is to be limited only by the following claims.

The invention claimed is:

1. A liquid composition that, when applied directly to water contained in a toilet bowl prior to use thereof, roils in the water, subsequently forms a sheen on the surface of the water, and thereafter reduces toilet odors during and following usage of the toilet bowl, the liquid composition comprising 60 to 70 weight percent diethylene glycol monoethyl ether, the balance of the liquid composition being a stabilizer and optionally fragrances, the stabilizer constituting about 0.5 weight percent of the liquid composition and containing about 40 to about 50 weight percent dipropylene glycol monomethyl ether.

2. The liquid composition according to claim 1, wherein the stabilizer further contains about 40 to about 50 weight percent ethoxylated alkyl phenol and less than 2 weight percent of a coumarin derivative.

3. The liquid composition according to claim 1, wherein the liquid composition comprises at least one fragrance.

4. The liquid composition according to claim 1, wherein the liquid composition consists of diethylene glycol monoethyl ether, fragrances, and the stabilizer.

5. The liquid composition according to claim 4, wherein the liquid composition consists of about 65 weight percent diethylene glycol monoethyl ether, about 34.5 weight percent fragrances, and about 0.5 weight percent stabilizer.

* * * * *